United States Patent [19]

Pissiotas et al.

[11] Patent Number: 5,039,329

[45] Date of Patent: Aug. 13, 1991

[54] 5-(PYRAZOL-1-1-YL)-BENZOIC ACID THIOL ESTERS WITH HERBICIDAL ACTION

[75] Inventors: Georg Pissiotas, Lörrach, Fed. Rep. of Germany; Hans Moser, Magden; Hans-Georg Brunner, Lausen, both of Switzerland

[73] Assignee: Ciba-Geigy Corporation, Ardsley, N.Y.

[21] Appl. No.: 528,662

[22] Filed: May 24, 1990

Related U.S. Application Data

[62] Division of Ser. No. 361,188, Jun. 5, 1989, Pat. No. 4,946,492.

[30] Foreign Application Priority Data

Jun. 16, 1988 [CH] Switzerland ............ 2322/88
Oct. 6, 1988 [CH] Switzerland ............ 3719/88

[51] Int. Cl.$^5$ .............. A01N 55/00; C07F 7/10
[52] U.S. Cl. ........................ 71/72; 71/92; 548/110
[58] Field of Search ............. 548/110; 71/92, 72

[56] References Cited

U.S. PATENT DOCUMENTS 4,752,325 6/1988 Haga ...................... 71/92
4,917,721 4/1990 Pissiotas ................. 71/96

FOREIGN PATENT DOCUMENTS 0347382 3/1990 European Pat. Off. .

Primary Examiner—Robert W. Ramsuer

Attorney, Agent, or Firm—Kevin T. Mansfield; Edward McC. Roberts

[57] ABSTRACT

Novel 5-(pyrazol-1-yl)-benzoic acid-thiolesters of the formula I have good selective-herbicidal action in pre- and postemergent application. They also inhibit plant growth. The esters correspond to formula I

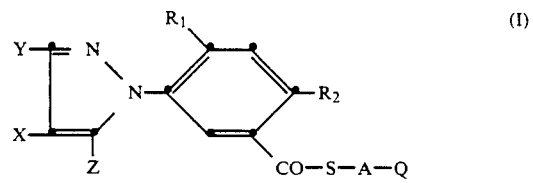

wherein
  X is hydrogen, halogen or $C_1$–$C_4$alkyl
  Y is $C_1$–$C_4$alkyl or
  X and Y together with the carbon atoms, to which they are bound, form a 5- to 6-membered ring, which can be substituted by methyl,
  Z is halogen, $C_1$–$C_6$alkyl, $C_1$–$C_4$alkoxy or $C_1$–$C_4$alkylthio
  $R_1$ is hydrogen or halogen
  $R_2$ is halogen
  A-Q together are hydroxyl or a radical —CH(COOR$_3$)COOR$_4$
  A is a $C_1$–$C_4$alkylene bridge
  Q, $R_3$ and $R_4$ have the meaning given in the disclosure.

The disclosure contains methods for synthesizing these esters and examples showing their use.

6 Claims, No Drawings

5-(PYRAZOL-1-1-YL)-BENZOIC ACID THIOL ESTERS WITH HERBICIDAL ACTION

This is a divisional of application Ser. No. 361,188 filed on June 5, 1989, now U.S. Pat. No. 4,946,492.

The present invention relates to novel 5-(pyrazol-1-yl)benzoic acid thiol esters of formula I with herbicidal and plant growth regulating properties, and to the preparation of these novel esters. The invention also relates to compositions which contain said novel compounds and to the use thereof for selectively controlling weeds or for regulating plant growth.

The novel 5-(pyrazol-1-yl)benzoic acid thiol esters are of formula I

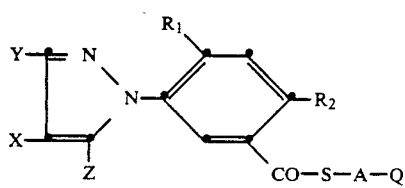

wherein
X hydrogen or halogen,
Y is $C_1$–$C_4$alkyl,
X and Y together with the carbon atoms, to which they are bound form also a 5- to 6-membered ring, which can be substituted by methyl,
Z Halogen, $C_1$–$C_6$alkyl, $C_1$–$C_4$alkoxy or $C_1$–$C_4$alkylthio,
$R_1$ is hydrogen or halogen,
$R_2$ is halogen,
A-Q taken together is hydrogen or a radical —CH(COCH$_3$)COOR$_4$,
A is a straight chain or branched $C_1$–$C_4$alkylene bridge, which is unsubstituted or mono- or polysubstituted by $C_1$–$C_4$alkoxy, $C_1$–$C_4$alkylthio or cyano,
Q is hydroxyl, halogen, cyano, thiocyanato (—SCN), $C_2$–$C_6$alkenyl, $C_2$–$C_6$haloalkenyl, $C_2$–$C_6$cyanoalkenyl, $C_2$–$C_4$alkynyl, or a radical —C($R_3$)=CH—COOR$_4$, —CH[N($R_3$)$_2$]COOR$_3$, —NR$_5$R$_6$, —CONR$_7$R$_8$, —Si(R$_{11}$)$_3$, —COOCH$_2$Si(CH$_3$)$_2$C$_1$–C$_6$alkyl, —COON=C(R$_9$)$_2$, —C(R$_3$)=(OR$_{10}$)$_2$, —PO(OR$_{12}$)—(O)$_p$R$_{12}$, —CON(R$_{13}$)SO$_2$C$_1$–C$_6$alkyl, —CON(R$_{13}$)SO$_2$C$_1$–C$_4$haloalkyl, $C_1$–$C_6$alkylcarbonyl, $C_1$–$C_6$alkoxycarbonyl, a radical benzoyl or benzylcarbonyl whose phenyl ring is unsubstituted, mono- or polysubstituted by halogen, $C_1$–$C_4$alkyl, $C_1$–$C_4$haloalkyl, $C_1$–$C_4$alkoxy, $C_1$–$C_4$haloalkoxy, cyano or nitro, Q is further a radical COOR$_{14}$, —CON(R$_3$)CH$_2$C(OC$_1$–C$_6$alkyl)$_2$ or $C_1$–$C_8$alkanoyloxy,
p is zero or 1,
$R_3$ is hydrogen, $C_1$–$C_6$alkyl or $C_2$–$C_6$alkoxyalkyl,
$R_4$ is $C_1$–$C_6$alkyl or $C_1$–$C_6$hydroxyalkyl,
$R_4$ and $R_5$ are independently of each other hydrogen, $C_1$–$C_6$alkyl, $C_2$–$C_6$alkoxyalkyl, $C_3$–$C_6$alkenyl, $C_3$–$C_6$alkynyl or $C_3$–$C_6$cycloalkyl, 2-furanylmethyl, 2-tetrahydrofuranylmethyl, 2-(5-methyl)-tetrahydrofuranylmethyl or 2-thienylmethyl
$R_5$ and $R_6$ form together with the nitrogen atom, to which they are bound also a radical pyrrolidino, piperidino oder morpholino, $R_7$ and $R_8$ are independently of each other hydrogen, $C_1$–$C_{12}$alkyl, $C_3$–$C_8$alkenyl, $C_3$–$C_6$alkynyl, $C_2$–$C_8$alkoxyalkyl, benzyl, phenyl or $C_1$–$C_4$cyanoalkyl,
$R_7$ and $R_8$ form together with the nitrogen atom, to which they are bound a radical pyrrolidino, piperidino, morpholino, thiomorpholino, 4-methylpiperazino, pyrazolidino, imidazolidino or 1,2,4-triazol, which is unsubstituted or mono- or disubstituted by $C_1$–$C_4$alkyl,
$R_9$ is $C_1$–$C_6$alkyl or two adjacent $R_9$ can form a $C_2$–$C_6$alkylene bridge,
$R_{10}$ is $C_1$–$C_4$alkyl or $C_1$–$C_4$haloalkyl or two adjacent $R_{10}$ from a 1,2-ethylene-, 1,3-propylene- or 1,2-cyclohexylene bridge,
$R_{11}$ is $C_1$–$C_6$alkyl or $C_1$–$C_6$alkoxy,
$R_{12}$ is hydrogen, $C_1$–$C_6$alkyl, $C_2$–$C_6$alkenyl or $C_3$–$C_6$alkynyl or $C_3$–$C_7$-cycloalkyl,
$R_{13}$ is $C_1$–$C_4$alkyl, or $C_3$–$C_7$cycloalkyl and
$R_{14}$ is hydrogen, $C_1$–$C_{12}$alkyl, $C_1$–$C_6$alkoxyalkyl, $C_3$–$C_7$alkenyl, $C_3$–$C_6$cyclo-alkyl, $C_3$–$C_5$alkenyloxy-$C_1$–$C_4$alkyl, $C_1$–$C_6$alkylthio-$C_1$–$C_4$alkyl or $C_1$–$C_4$dialkylamino-$C_1$–$C_4$alkyl Similar tetrahydrophthalimido-N-benzoic acid esters are described in the published European Patent applications EP-A 207,894 and 233,151. The thiolesters of this invention are structurally different and are distinguished from those by a more specific selective-herbicidal activity against grasses and weeds in cultures of cultivated plants.

Particularly active compounds are those of the formulae below, wherein Q has one of the following significances:

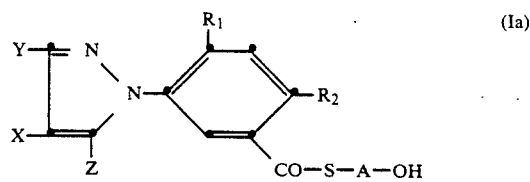

wherein A, $R_1$, $R_2$, X, Y and Z have the meaning given above;

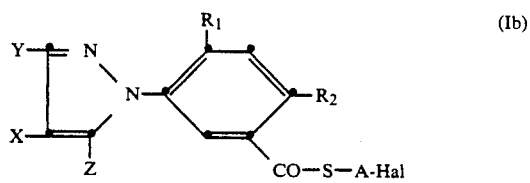

wherein A, $R_1$, $R_2$, X, Y and Z have the meaning given above and Hal is a halogen atom;

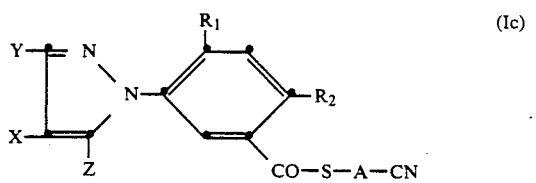

wherein A, $R_1$, $R_2$, X, Y and Z have the meaning given above;

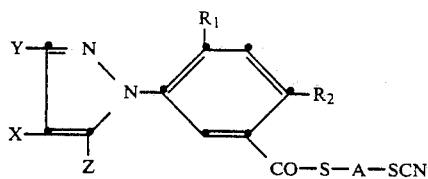 (Id)

wherein A, R₁, R₂, X, Y and Z have the meaning given above;

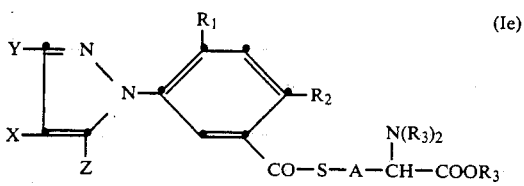 (Ie)

wherein A, R₁, R₂ the R₃ independently of each other, X, Y and Z have the meaning given above;

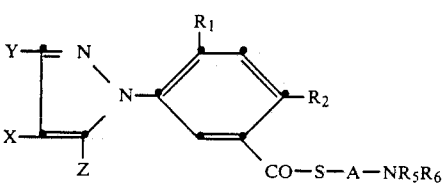 (If)

wherein A, R₁, R₂, R₅, R₆, X, Y and Z have the meaning given above;

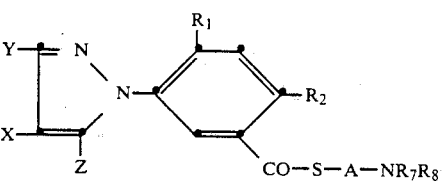 (Ig)

wherein A, R₁, R₂, R₇, R₈, X, Y and Z have the meaning given above;

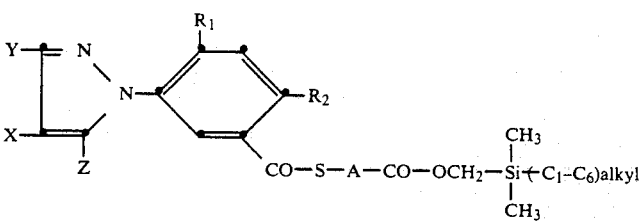 (Ih)

wherein A, R₁, R₂, X, Y and Z have the meaning given above;

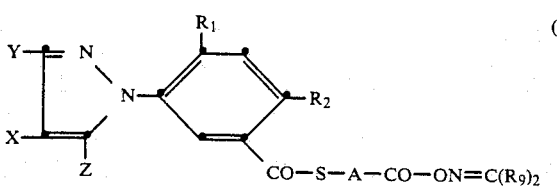 (Ii)

wherein A, R₁, R₂, R₉, X, Y and Z have the meaning given above;

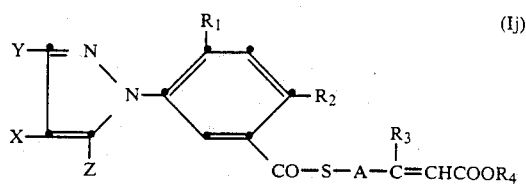 (Ij)

wherein A, R₁, R₂, R₃, R₄, X, Y and Z have the meaning given above;

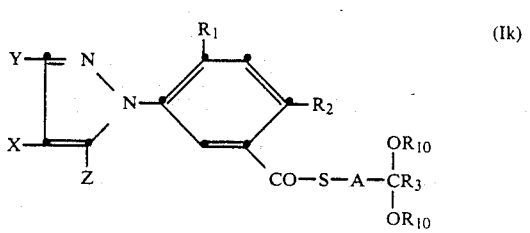 (Ik)

wherein A, R₁, R₂, R₃, R₁₀, X, Y and Z have the meaning given above;

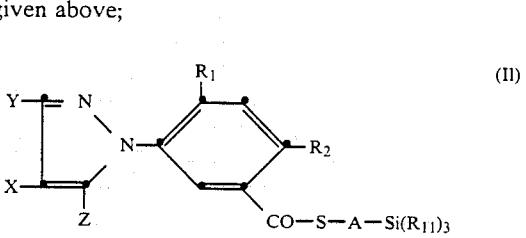 (Il)

wherein A, R₁, R₂, R₁₁, X, Y and Z have the meaning given above;

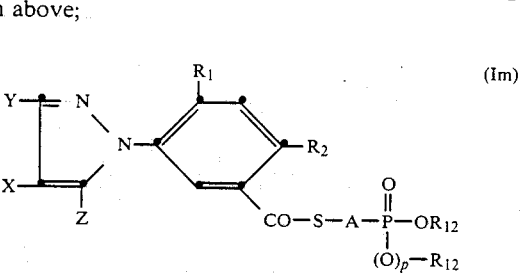 (Im)

wherein A, p, R₁, R₂, R₁₂, X, Y and Z have the meaning given above;

the compounds of the formula In

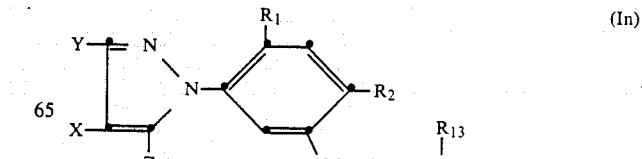 (In)

wherein A, $R_1$, $R_2$, $R_{13}$, X, Y and Z have the meaning given above;

the compounds of the formula Io

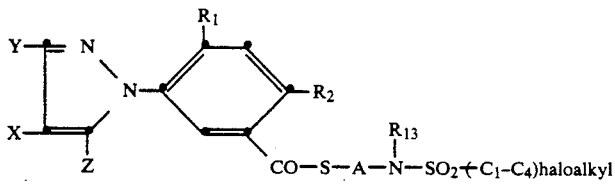
(Io)

wherein A, $R_1$, $R_2$, $R_{13}$, X, Y and Z have the meaning given above;

the compounds of the formula Ip

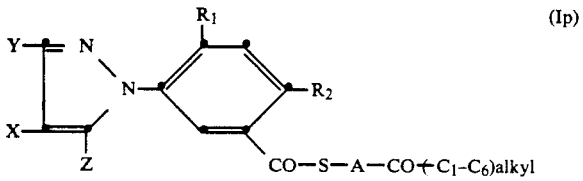
(Ip)

wherein A, $R_1$, $R_2$, X, Y and Z have the meaning given above;

the compounds of the formula Iq

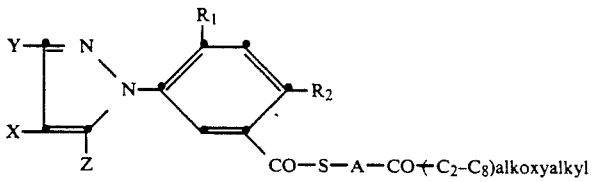
(Iq)

wherein A, $R_1$, $R_2$, X, Y and Z have the meaning given above;

the compounds of the formula Ir

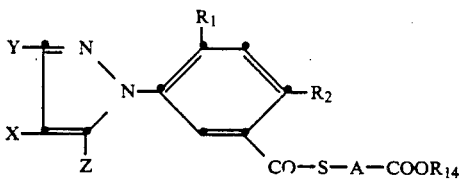
(Ir)

wherein A, $R_1$, $R_2$, $R_{14}$, X, Y and Z have the meaning given above;

and the compounds of the formula Is

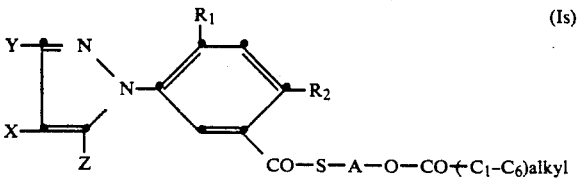
(Is)

wherein A, $R_1$, $R_2$, X, Y and Z have the meaning given above.

The invention comprises also the possible optically active isomers, diastereomers and enantiomers and their mixtures, in which the 5-(N-3,4,5,6-tetrahyphthalimido)benzoic-acid-thiol-esters of formula I may occur.

In the above definitions the expression halogen includes fluorine, chlorine, bromine or fluorine, especially fluorine, chlorine and bromine.

The expression alkyl, taken by itself or as part of a substituent includes straight-chained or branched radicals. Examples therefore are methyl, ethyl, n-propyl, isopropyl, n-butyl, sec. butyl, tert. butyl, isobutyl as well as the higher homologs thereof, pentyl, hexyl, heptyl, octyl, etc. together with their isomers. Cyanoalkyl radicals contains accordingly an additional carbon atom.

The $C_2$–$C_6$alkenyl- or $C_2$–$C_6$alkynyl radicals mentioned in the above definition include also straight-chained and branched radicals. Alkenyl includes especially 2-propenyl (allyl), 2-methyl-2-propenyl (methallyl), 1-methyl-2-propenyl, 2-butenyl and 3-butenyl, and alkynyl are preferably 2-propinyl (propargyl), 2-butinyl and 3-butinyl radicals. The alkenyl radicals of the definitions of Q, $R_6$ and $R_7$ are preferably allyl, methallyl or 2-butenyl and preferred alkynyl radicals are propargyl and 2-butynyl. If these unsaturated radicals are bound via an oxygen atom to the rest of the molecule, the radical is bound preferably via a saturated carbon atom to the oxygen.

The definition A includes methylene, 1,2-ethylene and 1,3-propylen as well as radicals which can be derived therefrom by substitution of one to two hydrogen atoms, such as 1,1-ethylene, isopropylene (2,2-propylene), 1,2-propylene, 2,3-butylene and 1,1-dimethyl-1,2-ethylene, 1,2-butylene, 1,3-butylene. Preferred radicals A are methylene, 1,2-ethylene, 1,2-propylene, and 2,3-butylene.

The generic definitions given in other substituents of the compounds of formula I comprise e.g. the following single radicals, which enumeration is not limiting the invention:

Haloalkyls are alkyl radicals which are partly or completely halogenated with identical or different halogen atoms and which correspond to the given range of the definition, such as e.g. trifluoromethyl, trichloromethyl, difluoromethyl, dichloromethyl, 2,2,2-trifluoroethyl and 1,1,1,3,3,3-hexafluoroprop-2-yl.

Alkoxy are to be understood radicals in the given range of the definition, such as preferably methoxy and ethoxy. $C_1$–$C_4$Alkoxy-$C_2$–$C_4$alkyl and $C_1$–$C_4$haloalkoxy in the given range of the definition are also to be understood as alkoxy radicals, such as e.g. methoxymethyl, methoxyethyl, difluoromethoxy, dichloromethoxy, trifluoromethoxy, chlorodifluoromethoxy and trichloromethoxy.

In the substituents, which consist of several basic elements, the parts can be chosen freely within the given range of the definition.

In accordance with the present invention, the novel 5-(pyrazol-1-yl)-benzoic acid thiol esters of formula I are prepared by reacting a 5-(pyrazol-1-yl)benzoic acid of the formula II

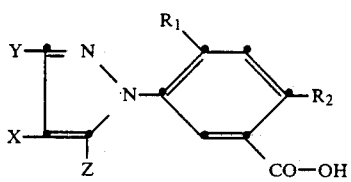

wherein $R_1$, $R_2$, X, Y and Z have the above given meaning, with a strong halogenating agent, to form the corresponding acid-halide of the formula III

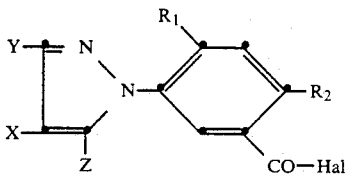

wherein $R_1$, $R_2$, X, Y and Z have the above given meaning, and Hal is a halogen atom, the acid halide is then converted in an inert organic solvent, in the presence of at least the equimolar amount of a base, with a mercaptan of the formula IV

 HS—A—Q (IV)

wherein

A and Q have the meaning given above to 5-(pyrazol-1-yl)benzoic acid-thiol ester of the formula I;

or by treating the acid-halide of the formula III in an inert organic solvent, in the presence of a base with hydrogen sulfide, to form the 5-(pyrazol-1-yl)thiolbenzoic acid of the formula V

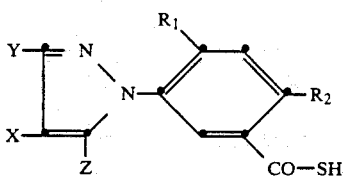

wherein $R_1$, $R_2$, X, Y and Z have the meaning given above, and converting this acid in an inert organic solvent, in the presence of the equimolar amount of a base, with an alkylhalide of the formula VI

 Hal—A—Q (VI)

wherein

A and Q have the meaning given above and Hal is a halogen atom, preferably chlorine or bromine to a 5-(pyrazol-1-yl)-benzoic acid-thiolester of the formula I.

Another way to prepare the 5-(pyrazol-1-yl)benzoic acid-thiol esters of formula I consists in nitrating a 5-(pyrazol-1-yl)-benzoic acid of the formula VII

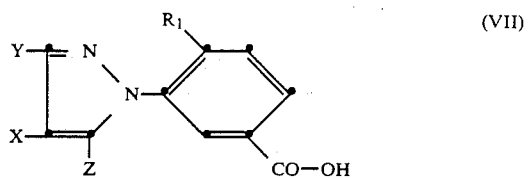

wherein $R_1$, X, Y and Z have the meaning given above, with a mixture of concentrated nitric acid and concentrated sulfuric acid, to obtain a 2-nitro-5-(pyrazol-1-yl)-benzoic acid of the formula VIII

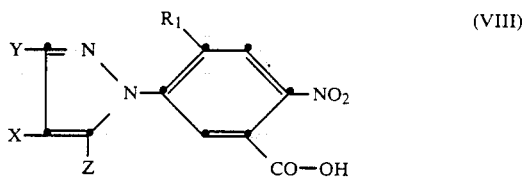

wherein $R_1$, X, Y and Z have the meaning given above, and reducing this nitrobenzoic acid in a way known per se by means of hydrogen to the 2-amino-5-(pyrazol-1-yl)-benzoic acid of the formula IX

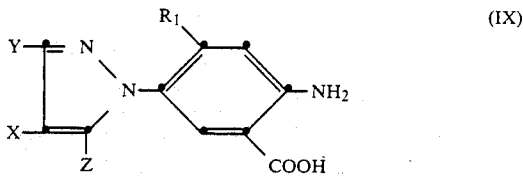

wherein $R_1$, X, Y and Z have the meaning given above, and diazotizing this aminobenzoic acid, in aqueous-acid medium, with sodium nitrate and a copper I-compound of the formula X

 $Cu^I$-Hal (X)

wherein Hal is chlorine, bromine or iodine, to the 5-(pyrazol-1-yl)-benzoic acid derivative of the formula II, which is then treated with a strong halogenating agent, as in the previous method to form the benzoic acid-halide of the formula III, which is further converted either directly or via the 5-(pyrazol-1-yl)-thiolbenzoic acid of the formula V, to the 5-(pyrazol-1-yl)-benzoic acid-thiolester of the formula I.

Suitable solvents or diluents for this reaction are higher boiling hydrocarbons, lower alkane acids and the esters thereof, higher boiling ketones and ethers. Examples of such solvents and diluents are toluene, xylene, acetic acid, ethyl acetate, isopropyl ether, tetrahydrofuran and methyl ethyl ketone.

The reaction takes place at a temperature in the range from 0° C. to the boiling point of the reaction mixture.

The reaction conditions in all described variants are similar.

The compounds of formula I are usually successfully applied at concentrations of 0.05 to 4 kg/ha, in particular 0.1 to 1 kg/ha.

When used at low rates of application, the compounds of formula I have good selective growth inhibiting and selective herbicidal properties which make them most suitable for use in crops of useful plants, preferably in cereals, cotton, maize and rice, especially however in soybeans. In some cases damage is also caused to weeds which have only been controlled up to now with total herbicides.

The mode of action of these compounds is unusual. Many are translocatable, i.e. they are absorbed by the plant and transported to other parts of it where they then exert their action. Thus, for example, it is possible to damage perennial weeds to the roots by surface treatment. Compared with other herbicides and growth regulators, the novel compounds of formula I are effective even when used at very low rates of application.

The compounds of formula I have in addition pronounced plant growth inhibiting properties. The growth of both monocots and dicots is inhibited.

Thus, for example, the compounds of formula I selectively inhibit the growth of leguminosae which are frequently planted as cover crops in tropical regions, so that, while soil erosion between cultivated plants is prevented, the cover crops cannot compete with the cultivated plants.

Inhibition of the vegetative growth of many cultivated plants permits more plants to be sown in a crop area, so that a higher yield may be obtained per unit of area. A further mechanism of yield increase using growth inhibitors resides in the fact that nutrients are able increasingly to promote flower formation and fruiting, whereas vegetative growth is inhibited.

The compounds of formula I can also be used for defoliating and desiccating crops of cotton and potatoes. By treating the crops at the moment of ripening, the harvesting of the cotton capsules or of the tubers is greatly facilitated when the leaves fall off and/or shrivel up or when the shrubs shrivel up.

At higher rates of application of compounds of formula I, all tested plants are so severely damaged in their development that they die.

The invention also relates to herbicidal and plant growth regulating compositions which contain a novel compound of formula I, and also to methods of controlling weeds pre- and postemergence and of inhibiting the growth of monocots and dicots, especially grasses, tropical cover crops and tobacco plant suckers.

The compounds of formula I are used in unmodified form or, preferably, together with the adjuvants conventionally employed in the art of formulation, and are therefore formulated in known manner e.g. to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstitued or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product.

Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 10 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, such as polyoxyethylene sorbitan trioleate, are also suitable non-ionic surfactants.

Cationic surfactants are preferably quaternary ammonium salts which contain, as N-substituent, at least one $C_8$-$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described e.g. in the following publications:

"McCutcheon's Detergents and Emulsifiers Annual", MC Publishing Corp., Ridgewood, N.J. 1981; H. Stache, "Tensid-Taschenbuch" (Handbook of Surfactants), C. Hanser Verlag, Munich & Vienna, 1981.

The herbicidal preparations usually contain 0.1 to 95%, preferably 0.1 to 80%, of a compound of formula I, 1 to 99.9% of a solid or liquid adjuvant, and 0 to 25%, preferably 0.1 to 25%, of a surfactant.

Preferred formulations are composed in particular of the following constituents (% = percentage by weight):

| Emulsifiable concentrates | |
|---|---|
| compound of formula I: | 1 to 20% preferably 5 to 10% |
| surfactant: | 5 to 30%, preferably 10 to 20% |
| liquid carrier: | 50 to 94%, preferably 70 to 85% |

| Dusts | |
|---|---|
| compound of formula I: | 0.1 to 10%, preferably 0.1 to 1% |
| solid carrier: | 99.9 to 90%, preferably 99.9 to 99% |

| Suspension concentrates | |
|---|---|
| compound of formula I: | 5 to 75%, preferably 10 to 50% |
| water: | 94 to 25%, preferably 90 to 30% |
| surfactant: | 1 to 40%, preferably 2 to 30% |

| Wettable powders | |
|---|---|
| compound of formula I: | 0.5 to 90%, preferably 1 to 80% |
| surfactant: | 0.5 to 20%, preferably 1 to 15% |
| solid carrier: | 5 to 95%, preferably 15 to 90% |

| Granulates | |
|---|---|
| compound of formula I: | 0.5 to 30%, preferably 3 to 15% |
| solid carrier: | 99.5 to 70%, preferably 97 to 85%. |

Whereas commercial products will be preferably formulated as concentrates, the end user will normally employ dilute formulations. The formulations can be diluted to a concentration as low as 0.001% of active ingredient. The rates of application are usually from 0.005 to 5 kg a.i./ha.

The compositions may also contain further ingredients such as stabilisers, antifoams, viscosity regulators, binders, tackifiers, as well as fertilisers and other compounds for obtaining special effects.

The following Example illustrates the preparation of a compound of the formula I. Further compounds prepared in corresponding manner are listed in the subsequent Tables. Temperatures are given in degrees centigrade, pressures in millibar (mbar).

EXAMPLE 1

Preparation of 5-[2-(3-chloro-4,5,6,7-tetrahydro-2H-indazolyl)]-2-chloro-4-fluorobenzoic acid-(methoxy carbonylmethylthiol)ester

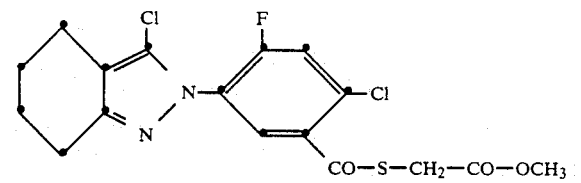

A solution of 3.5 g of 5-[2-(3-chloro-4,5,6,7-tetrahydro-2H-indazolyl)]-2-chloro-4-fluorobenzoic acid chloride in 30 ml of toluene is added slowly, while stirring at room temperature, to a mixture of 1.1 g of thioglycolic acid-methyl ester and 1.5 ml of triethylamine in 50 ml of toluene. After everything is added, the reaction mixture is stirred for another 3 hours at room temperature. The triethylamine-hydrochloride is then filtered off, the filtrate is concentrated under vacuum. The residue is the title product which melts at 98°-99° C.

In analogy to this example the compounds listed in tables 1 to 4 are prepared.

TABLE 1

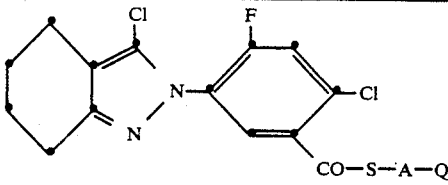

| No. | A—Q | phys. data |
|---|---|---|
| 1.001 | —CH$_2$—COOH | |
| 1.002 | —CH$_2$—COOCH$_3$ | m.p. 98–99° |
| 1.003 | —CH$_2$—COOC$_2$H$_5$ | n$_D^{23}$ 1,5869 |
| 1.004 | —CH$_2$—COOC$_3$H$_7$-n | |
| 1.005 | —CH$_2$—COOCH(CH$_3$)$_2$ | n$_D^{23}$ 1,5799 |
| 1.006 | —CH$_2$—COOC$_4$H$_9$-n | n$_D^{23}$ 1,5748 |
| 1.007 | —CH$_2$—COOCH$_2$CH(CH$_3$)$_2$ | |
| 1.008 | —CH$_2$—COOCH(CH$_3$)C$_2$H$_5$ | |
| 1.009 | —CH$_2$—COOC(CH$_3$)$_3$ | |
| 1.010 | —CH$_2$—COO(CH$_2$)$_9$CH$_3$ | |
| 1.011 | —CH$_2$—COOCH$_2$CH$_2$OCH$_3$ | n$_D^{23}$ 1,5812 |
| 1.012 | —CH$_2$—COOCH$_2$CH$_2$OC$_2$H$_5$ | |
| 1.013 | —CH$_2$—COOCH$_2$CH$_2$OC$_3$H$_7$-n | |
| 1.014 | —CH$_2$—COO Cyclohexyl | n$_D^{23}$ 1,5702 |
| 1.015 | —CH$_2$—COOCH$_2$CH$_2$OCH$_2$CH=CH$_2$ | |
| 1.016 | —CH$_2$—COOC(CH$_3$)$_2$CN | |
| 1.017 | —CH$_2$COOCH$_2$CH$_2$SCH$_3$ | |
| 1.018 | —CH$_2$COOCH(CH$_3$)CH$_2$N(CH$_3$)$_2$ | |
| 1.019 | —CH(CH$_3$)COOH | m.p. 144–146° |
| 1.020 | —CH(CH$_3$)COOCH$_3$ | n$_D^{20}$ 1,5855 |
| 1.021 | —CH(CH$_3$)COOC$_2$H$_5$ | n$_D^{22}$ 1,5722 |
| 1.022 | —CH(CH$_3$)COOC$_3$H$_7$-n | |
| 1.023 | —CH(CH$_3$)COOCH(CH$_3$)$_2$ | n$_D^{22}$ 1,5705 |
| 1.024 | —CH(CH$_3$)COOC$_4$H$_9$-n | |
| 1.025 | —CH(CH$_3$)COOCH$_2$CH(CH$_3$)$_2$ | |
| 1.026 | —CH(CH$_3$)COOCH(CH$_3$)C$_2$H$_5$ | |
| 1.027 | —CH(CH$_3$)COOC(CH$_3$)$_3$ | n$_D^{22}$ 1,5418 |
| 1.028 | —CH(CH$_3$)COO—C$_5$H$_{11}$-n | |
| 1.029 | —CH(CH$_3$)COOCH$_2$CH$_2$OCH$_3$ | |
| 1.030 | —CH(CH$_3$)COOCH$_2$CH$_2$OC$_2$H$_5$ | |
| 1.031 | —CH(CH$_3$)COOCH$_2$CH$_2$OC$_3$H$_7$-n | |
| 1.032 | —CH(CH$_3$)COOCH$_2$CH$_2$OCH$_2$CH=CH$_2$ | |
| 1.033 | —CH(CH$_3$)COOC(CH$_3$)$_2$CN | |
| 1.034 | —CH(CH$_3$)COOCH$_2$CH$_2$SCH$_3$ | |
| 1.035 | —CH(CH$_3$)CH$_2$OH | |
| 1.036 | —CH(CH$_3$)CN | |
| 1.037 | —C$_2$H$_4$OH | |
| 1.038 | —CH(CH$_3$)CH$_2$Cl | |
| 1.039 | —C$_2$H$_4$Cl | |
| 1.040 | —CH$_2$CN | |
| 1.041 | —CH$_2$C(CH$_3$)$_2$OH | |
| 1.042 | —CH$_2$SCN | |
| 1.043 | —C$_2$H$_4$CN | |
| 1.044 | —CH(CH$_3$)CH$_2$CN | |
| 1.045 | —CH(CH$_2$OCH$_3$)COOCH$_3$ | |
| 1.046 | —CH$_2$CH(OCH$_3$)COOCH$_3$ | |
| 1.047 | —CH(CH$_3$)COOC$_2$H$_4$OCH$_2$CH=CH$_2$ | |
| 1.048 | —CH(CN)CH$_2$OCH$_3$ | |
| 1.049 | —CH$_2$CH(SCH$_3$)COOCH$_3$ | |
| 1.050 | —CH$_2$CH=CH$_2$ | |
| 1.051 | —CH$_2$CH=CHCl | |
| 1.052 | —CH$_2$CCl=CH$_2$ | |
| 1.053 | —CH$_2$CH=CHCN | |
| 1.054 | —CH$_2$C≡CH | |
| 1.055 | —CH$_2$C(CH$_3$)=CHCOOCH$_3$ | |
| 1.056 | —C$_2$H$_4$N(CH$_3$)$_2$ | |
| 1.057 | —C$_2$H$_4$-pyrrolidino | |
| 1.058 | —C$_2$H$_4$-piperidino | |
| 1.059 | —C$_2$H$_4$-morpholino | |
| 1.060 | —CH[N(CH$_3$)$_2$]COOCH$_3$ | |
| 1.061 | —CH(CH$_3$)CH$_2$N(CH$_3$)$_2$ | |
| 1.062 | —CH(CH$_3$)CO-piperidino | |
| 1.063 | —CH(CH$_3$)CO-pyrrolidino | |
| 1.064 | —CH(CH$_3$)CO-4-methylpiperazino | |
| 1.065 | —CH(CH$_3$)CO-morpholino | |
| 1.066 | —CH(CH$_3$)CO-2-methylmorpholino | |
| 1.067 | —CH(CH$_3$)CO-2,6-dimethylmorpholino | |
| 1.068 | —CH(CH$_3$)CO-2-methylpiperidino | |
| 1.069 | —CH(CH$_3$)CO-3-methylpiperidino | |
| 1.070 | —CH(CH$_3$)CO-4-methylpiperidino | |
| 1.071 | —CH(CH$_3$)CO—N(CH$_3$)CH$_2$CN | |
| 1.072 | —CH(CH$_3$)CO—N(CH$_2$CH=CH$_2$)$_2$ | |

TABLE 1-continued

[Structure: bicyclic pyrazoline with Cl, CH₃ substituents, N-N linked to phenyl ring bearing F, Cl, and CO—S—A—Q]

| No. | A—Q | phys. data |
|---|---|---|
| 1.073 | —CH(CH₃)CO—OCH₂Si(CH₃)₃ | |
| 1.074 | —CH(CH₃)CO—OC₂H₄Si(CH₃)₃ | |
| 1.075 | —CH(CH₃)CO—ON=C(CH₃)₂ | |
| 1.076 | —CH(CH₃)CO—ON=cyclopentyl | |
| 1.077 | —CH(CH₃)CO—ON=cyclohexyl | |
| 1.078 | -1,3-dioxolan-2-yleth-1-yl | |
| 1.079 | -1,3-dioxolan-2-ylmethyl | |
| 1.080 | -4-methyl-1,3-dioxolan-2-ylmethyl | |
| 1.081 | -1,3-dioxolan-2-ylpropyl | |
| 1.082 | -2-methyl-1,3-dioxolan-2-ylpropyl | |
| 1.083 | —C₂H₄C(OCH₃)₂ | |
| 1.084 | —C₂H₄C(OC₂H₅)₂ | |
| 1.085 | —CH(CH₃)C(OC₂H₅)₂ | |
| 1.086 | —CH(CH₃)C(OCH₃)₂ | |
| 1.087 | -2-methyl-1,3-dioxolan-2-ylmethyl | |
| 1.088 | —C₂H₄Si(OC₂H₅)₃ | |
| 1.089 | —CH₂Si(CH₃)₃ | $n_D^{23}$ 1,5801 |
| 1.090 | —CH(CH₃)Si(CH₃)₃ | |
| 1.091 | —C₂H₄Si(CH₃)₃ | |
| 1.092 | —CH(CH₃)CH₂Si(CH₃)₃ | |
| 1.093 | —CH(CH₃)PO(OC₂H₅)₂ | |
| 1.094 | —CH(CH₃)PO(CH₃)OC₂H₅ | |
| 1.095 | —CH(CH₃)CON(CH₃)SO₂CH₃ | |
| 1.096 | —CH(CH₃)CON(CH₃)SO₂CH₂Cl | |
| 1.097 | —CH₂CON(CH₃)SO₂CH₃ | |
| 1.098 | —CH(CH₃)CON(CH₂CH=CH₂)SO₂CH₃ | |
| 1.099 | —CH(CH₃)CON(cyclopropyl)SO₂CH₃ | |
| 1.100 | —CH(CH₃)CON[CH(CH₃)₂]SO₂CH₃ | |
| 1.101 | —CH₂COCH₃ | |
| 1.102 | —CH₂CO benzyl | |
| 1.103 | —CH₂CO phenyl | |
| 1.104 | —CH₂COCH₂OCH₃ | |
| 1.105 | —CH(CH₃)COCH₃ | |
| 1.106 | —CH(CH₃)COCH₂COOCH₃ | |
| 1.107 | —CH(COCH₃)COOC₂H₅ | |
| 1.108 | —CH(CH₃)COOCH(CH₃)CH₂SCH₃ | |
| 1.109 | —CH(CH₃)COOCH(CH₃)CH₂SC₂H₅ | |
| 1.110 | —CH(CH₃)COOCH(CH₃)CH₂SC₃H₇-n | |
| 1.111 | —CH(CH₃)COOCH(CH₃)CH₂SCH(CH₃)₂ | |
| 1.112 | —CH(CH₃)COOCH(CH₃)CH₂SC₄H₉-n | |
| 1.113 | —CH(CH₃)COOCH(CH₃)CH₂SC(CH₃)₃ | |
| 1.114 | —CH(CH₃)COOCH(CH₃)CH₂SCH(CH₃)C₂H₅ | |
| 1.115 | —CH(CH₃)CON(CH₃)CH₂CH(OCH₃)₂ | |
| 1.116 | —CH(CH₃)CON(CH₃)CH₂CH(OC₂H₅)₂ | |
| 1.117 | —CH(CH₃)COOC₂H₄OCH₂CH=CH₂ | |
| 1.118 | —CH(COCH₃)₂ | |
| 1.119 | —CH(CN)COOCH₃ | |
| 1.120 | —CH(OCH₃)COOCH₃ | |
| 1.121 | —CH₂—CH₂—N(CH₃)(CH₃) | $n_D^{25}$ 1,5828 |
| 1.122 | —C₂H₄COOCH₃ | $n_D^{25}$ 1,5655 |
| 1.123 | —C₂H₄COOC₂H₅ | $n_D^{25}$ 1,5615 |

TABLE 2

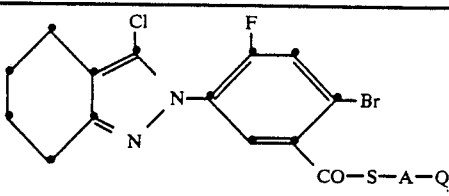

| No. | A—Q | phys. data |
|---|---|---|
| 2.001 | —CH₂—COOH | |
| 2.002 | —CH₂—COOCH₃ | |
| 2.003 | —CH₂—COOC₂H₅ | |
| 2.004 | —CH₂—COOC₃H₇-n | |
| 2.005 | —CH₂—COOCH(CH₃)₂ | |
| 2.006 | —CH₂—COOC₄H₉-n | |
| 2.007 | —CH₂—COOCH₂CH(CH₃)₂ | |
| 2.008 | —CH₂—COOCH(CH₃)C₂H₅ | |
| 2.009 | —CH₂—COOC(CH₃)₃ | |
| 2.010 | —CH₂—COO(CH₂)₉CH₃ | |
| 2.011 | —CH₂—COOCH₂CH₂OCH₃ | |
| 2.012 | —CH₂—COOCH₂CH₂OC₂H₅ | |
| 2.013 | —CH₂—COOCH₂CH₂OC₃H₇-n | |
| 2.014 | —CH₂—COO Cyclohexyl | |
| 2.015 | —CH₂—COOCH₂CH₂OCH₂CH=CH₂ | |
| 2.016 | —CH₂—COOC(CH₃)₂CN | |
| 2.017 | —CH₂COOCH₂CH₂SCH₃ | |
| 2.018 | —CH₂—COOCH(CH₃)CH₂N(CH₃)₂ | |
| 2.019 | —CH(CH₃)COOH | |
| 2.020 | —CH(CH₃)COOCH₃ | |
| 2.021 | —CH(CH₃)COOC₂H₅ | |
| 2.022 | —CH(CH₃)COOC₃H₇-n | |
| 2.023 | —CH(CH₃)COOCH(CH₃)₂ | |
| 2.024 | —CH(CH₃)COOC₄H₉-n | |
| 2.025 | —CH(CH₃)COOCH₂CH(CH₃)₂ | |
| 2.026 | —CH(CH₃)COOCH(CH₃)C₂H₅ | |
| 2.027 | —CH(CH₃)COOC(CH₃)₃ | |
| 2.028 | —CH(CH₃)COO—C₅H₁₁-n | |
| 2.029 | —CH(CH₃)COOCH₂CH₂OCH₃ | |
| 2.030 | —CH(CH₃)COOCH₂CH₂OC₂H₅ | |
| 2.031 | —CH(CH₃)COOCH₂CH₂OC₃H₇-n | |
| 2.032 | —CH(CH₃)COOCH₂CH₂OCH₂CH=CH₂ | |
| 2.033 | —CH(CH₃)COOC(CH₃)₂CN | |
| 2.034 | —CH(CH₃)COOCH₂CH₂SCH₃ | |
| 2.035 | —CH(CH₃)CH₂OH | |
| 2.036 | —CH(CH₃)CN | |
| 2.037 | —C₂H₄OH | |
| 2.038 | —CH(CH₃)CH₂Cl | |
| 2.039 | —C₂H₄Cl | |
| 2.040 | —CH₂CN | |
| 2.041 | —CH₂C(CH₃)₂OH | |
| 2.042 | —CH₂SCN | |
| 2.043 | —C₂H₄CN | |
| 2.044 | —CH(CH₃)CH₂CN | |
| 2.045 | —CH(CH₂OCH₃)COOCH₃ | |
| 2.046 | —CH₂CH(OCH₃)COOCH₃ | |
| 2.047 | —CH(CH₃)COOC₂H₄OCH₂CH=CH₂ | |
| 2.048 | —CH(CN)CH₂OCH₃ | |
| 2.049 | —CH₂CH(SCH₃)COOCH₃ | |
| 2.050 | —CH₂CH=CH₂ | |
| 2.051 | —CH₂CH=CHCl | |
| 2.052 | —CH₂CCl=CH₂ | |
| 2.053 | —CH₂CH=CHCN | |
| 2.054 | —CH₂C≡CH | |
| 2.055 | —CH₂C(CH₃)=CHCOOCH₃ | |
| 2.056 | —C₂H₄N(CH₃)₂ | |
| 2.057 | —C₂H₄-pyrrolidino | |
| 2.058 | —C₂H₄-piperidino | |
| 2.059 | —C₂H₄-morpholino | |
| 2.060 | —CH[N(CH₃)₂]COOCH₃ | |
| 2.061 | —CH(CH₃)CH₂N(CH₃)₂ | |
| 2.062 | —CH(CH₃)CO-piperidino | |
| 2.063 | —CH(CH₃)CO-pyrrolidino | |
| 2.064 | —CH(CH₃)CO-4-methylpiperazino | |
| 2.065 | —CH(CH₃)CO-morpholino | |
| 2.066 | —CH(CH₃)CO-2-methylmorpholino | |
| 2.067 | —CH(CH₃)CO-2,6-dimethylmorpholino | |
| 2.068 | —CH(CH₃)CO-2-methylpiperidino | |
| 2.069 | —CH(CH₃)CO-3-methylpiperidino | |
| 2.070 | —CH(CH₃)CO-4-methylpiperidino | |
| 2.071 | —CH(CH₃)CO—N(CH₃)CH₂CN | |

TABLE 2-continued

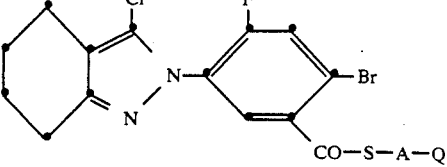

| No. | A—Q | phys. data |
|---|---|---|
| 2.072 | —CH(CH₃)CO—N(CH₂CH=CH₂)₂ | |
| 2.073 | —CH(CH₃)CO—OCH₂Si(CH₃)₃ | |
| 2.074 | —CH(CH₃)CO—OC₂H₄Si(CH₃)₃ | |
| 2.075 | —CH(CH₃)CO—ON=C(CH₃)₂ | |
| 2.076 | —CH(CH₃)CO—ON=cyclopentyl | |
| 2.077 | —CH(CH₃)CO—ON=cyclohexyl | |
| 2.078 | -1,3-dioxolan-2-yleth-1-yl | |
| 2.079 | -1,3-dioxolan-2-ylmethyl | |
| 2.080 | -4-methyl-1,3-dioxolan-2-ylmethyl | |
| 2.081 | -1,3-dioxolan-2-ylpropyl | |
| 2.082 | -2-methyl-1,3-dioxolan-2-ylpropyl | |
| 2.083 | —C₂H₄C(OCH₃)₂ | |
| 2.084 | —C₂H₄C(OC₂H₅)₂ | |
| 2.085 | —CH(CH₃)C(OC₂H₅)₂ | |
| 2.086 | —CH(CH₃)C(OCH₃)₂ | |
| 2.087 | -2-methyl-1,3-dioxolan-2-ylmethyl | |
| 2.088 | —C₂H₄Si(OC₂H₅)₃ | |
| 2.089 | —CH₂Si(CH₃)₃ | |
| 2.090 | —CH(CH₃)Si(CH₃)₃ | |
| 2.091 | —C₂H₄Si(CH₃)₃ | |
| 2.092 | —CH(CH₃)CH₂Si(CH₃)₃ | |
| 2.093 | —CH(CH₃)PO(OC₂H₅)₂ | |
| 2.094 | —CH(CH₃)PO(CH₃)OC₂H₅ | |
| 2.095 | —CH(CH₃)CON(CH₃)SO₂CH₃ | |
| 2.096 | —CH(CH₃)CON(CH₃)SO₂CH₂Cl | |
| 2.097 | —CH₂CON(CH₃)SO₂CH₃ | |
| 2.098 | —CH(CH₃)CON(CH₂CH=CH₂)SO₂CH₃ | |
| 2.099 | —CH(CH₃)CON(cyclopropyl)SO₂CH₃ | |
| 2.100 | —CH(CH₃)CON[CH(CH₃)₂]SO₂CH₃ | |
| 2.101 | —CH₂COCH₃ | |
| 2.102 | —CH₂CO benzyl | |
| 2.103 | —CH₂CO phenyl | |
| 2.104 | —CH₂COCH₂OCH₃ | |
| 2.105 | —CH(CH₃)COCH₃ | |
| 2.106 | —CH(CH₃)COCH₂COOCH₃ | |
| 2.107 | —CH(COCH₃)COOC₂H₅ | |
| 2.108 | —CH(CH₃)COOCH(CH₃)CH₂SCH₃ | |
| 2.109 | —CH(CH₃)COOCH(CH₃)CH₂SC₂H₅ | |
| 2.110 | —CH(CH₃)COOCH(CH₃)CH₂SC₃H₇-n | |
| 2.111 | —CH(CH₃)COOCH(CH₃)CH₂SCH(CH₃)₂ | |
| 2.112 | —CH(CH₃)COOCH(CH₃)CH₂SC₄H₉-n | |
| 2.113 | —CH(CH₃)COOCH(CH₃)CH₂SC(CH₃)₃ | |
| 2.114 | —CH(CH₃)COOCH(CH₃)CH₂SCH(CH₃)C₂H₅ | |
| 2.115 | —CH(CH₃)CON(CH₃)CH₂CH(OCH₃)₂ | |
| 2.116 | —CH(CH₃)CON(CH₃)CH₂CH(OC₂H₅)₂ | |
| 2.117 | —CH(CH₃)COOC₂H₄OCH₂CH=CH₂ | |
| 2.118 | —CH(COCH₃)₂ | |
| 2.119 | —CH(CN)COOCH₃ | |
| 2.120 | —CH(OCH₃)COOCH₃ | |
| 2.121 | —CH₂CH₂COOC₂H₅ | |
| 2.122 | —CH₂CH₂COOCH₃ | |

TABLE 3

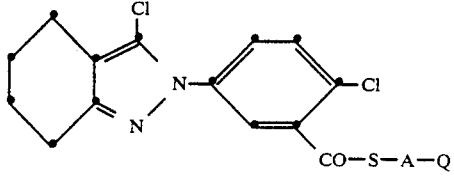

| No. | A—Q | phys. data |
|---|---|---|
| 3.001 | —CH₂—COOH | |
| 3.002 | —CH₂—COOCH₃ | |
| 3.003 | —CH₂—COOC₂H₅ | |
| 3.004 | —CH₂—COOC₃H₇-n | |

TABLE 3-continued

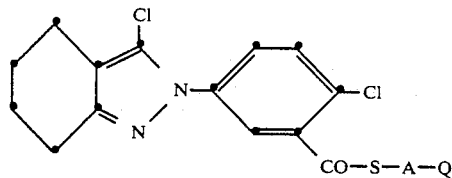

| No. | A—Q | phys. data |
|---|---|---|
| 3.005 | —CH$_2$—COOCH(CH$_3$)$_2$ | |
| 3.006 | —CH$_2$—COOC$_4$H$_9$-n | |
| 3.007 | —CH$_2$—COOCH$_2$CH(CH$_3$)$_2$ | |
| 3.008 | —CH$_2$—COOCH(CH$_3$)C$_2$H$_5$ | |
| 3.009 | —CH$_2$—COOC(CH$_3$)$_3$ | |
| 3.010 | —CH$_2$—COO(CH$_2$)$_9$CH$_3$ | |
| 3.011 | —CH$_2$—COOCH$_2$CH$_2$OCH$_3$ | |
| 3.012 | —CH$_2$—COOCH$_2$CH$_2$OC$_2$H$_5$ | |
| 3.013 | —CH$_2$—COOCH$_2$CH$_2$OC$_3$H$_7$-n | |
| 3.014 | —CH$_2$—COO Cyclohexyl | |
| 3.015 | —CH$_2$—COOCH$_2$CH$_2$OCH$_2$CH=CH$_2$ | |
| 3.016 | —CH$_2$—COOC(CH$_3$)$_2$CN | |
| 3.017 | —CH$_2$COOCH$_2$CH$_2$SCH$_3$ | |
| 3.018 | —CH$_2$—COOCH(CH$_3$)CH$_2$N(CH$_3$)$_2$ | |
| 3.019 | —CH(CH$_3$)COOH | |
| 3.020 | —CH(CH$_3$)COOCH$_3$ | |
| 3.021 | —CH(CH$_3$)COOC$_2$H$_5$ | |
| 3.022 | —CH(CH$_3$)COOC$_3$H$_7$-n | |
| 3.023 | —CH(CH$_3$)COOCH(CH$_3$)$_2$ | |
| 3.024 | —CH(CH$_3$)COOC$_4$H$_9$-n | |
| 3.025 | —CH(CH$_3$)COOCH$_2$CH(CH$_3$)$_2$ | |
| 3.026 | —CH(CH$_3$)COOCH(CH$_3$)C$_2$H$_5$ | |
| 3.027 | —CH(CH$_3$)COOC(CH$_3$)$_3$ | |
| 3.028 | —CH(CH$_3$)COO—C$_5$H$_{11}$-n | |
| 3.029 | —CH(CH$_3$)COOCH$_2$CH$_2$OCH$_3$ | |
| 3.030 | —CH(CH$_3$)COOCH$_2$CH$_2$OC$_2$H$_5$ | |
| 3.031 | —CH(CH$_3$)COOCH$_2$CH$_2$OC$_3$H$_7$-n | |
| 3.032 | —CH(CH$_3$)COOCH$_2$CH$_2$OCH$_2$CH=CH$_2$ | |
| 3.033 | —CH(CH$_3$)COOC(CH$_3$)$_2$CN | |
| 3.034 | —CH(CH$_3$)COOCH$_2$CH$_2$SCH$_3$ | |
| 3.035 | —CH(CH$_3$)CH$_2$OH | |
| 3.036 | —CH(CH$_3$)CN | |
| 3.037 | —C$_2$H$_4$OH | |
| 3.038 | —CH(CH$_3$)CH$_2$Cl | |
| 3.039 | —C$_2$H$_4$Cl | |
| 3.040 | —CH$_2$CN | |
| 3.041 | —CH$_2$C(CH$_3$)$_2$OH | |
| 3.042 | —CH$_2$SCN | |
| 3.043 | —C$_2$H$_4$CN | |
| 3.044 | —CH(CH$_3$)CH$_2$CN | |
| 3.045 | —CH(CH$_2$OCH$_3$)COOCH$_3$ | |
| 3.046 | —CH$_2$CH(OCH$_3$)COOCH$_3$ | |
| 3.047 | —CH(CH$_3$)COOC$_2$H$_4$OCH$_2$CH=CH$_2$ | |
| 3.048 | —CH(CN)CH$_2$OCH$_3$ | |
| 3.049 | —CH$_2$CH(SCH$_3$)COOCH$_3$ | |
| 3.050 | —CH$_2$CH=CH$_2$ | |
| 3.051 | —CH$_2$CH=CHCl | |
| 3.052 | —CH$_2$CCl=CH$_2$ | |
| 3.053 | —CH$_2$CH=CHCN | |
| 3.054 | —CH$_2$C≡CH | |
| 3.055 | —CH$_2$C(CH$_3$)=CHCOOCH$_3$ | |
| 3.056 | —C$_2$H$_4$N(CH$_3$)$_2$ | |
| 3.057 | —C$_2$H$_4$-pyrrolidino | |
| 3.058 | —C$_2$H$_4$-piperidino | |
| 3.059 | —C$_2$H$_4$-morpholino | |
| 3.060 | —CH[N(CH$_3$)$_2$]COOCH$_3$ | |
| 3.061 | —CH(CH$_3$)CH$_2$N(CH$_3$)$_2$ | |
| 3.062 | —CH(CH$_3$)CO-piperidino | |

TABLE 3-continued

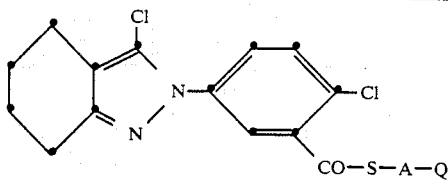

| No. | A—Q | phys. data |
|---|---|---|
| 3.063 | —CH(CH$_3$)CO-pyrrolidino | |
| 3.064 | —CH(CH$_3$)CO-methylpiperazino | |
| 3.065 | —CH(CH$_3$)CO-morpholino | |
| 3.066 | —CH(CH$_3$)CO-2-methylmorpholino | |
| 3.067 | —CH(CH$_3$)CO-2,6-dimethylmorpholino | |
| 3.068 | —CH(CH$_3$)CO-2-methylpiperidino | |
| 3.069 | —CH(CH$_3$)CO-3-methylpiperidino | |
| 3.070 | —CH(CH$_3$)CO-4-methylpiperidino | |
| 3.071 | —CH(CH$_3$)CO—N(CH$_3$)CH$_2$CN | |
| 3.072 | —CH(CH$_3$)CO—N(CH$_2$CH=CH$_2$)$_2$ | |
| 3.073 | —CH(CH$_3$)CO—OCH$_2$Si(CH$_3$)$_3$ | |
| 3.074 | —CH(CH$_3$)CO—OC$_2$H$_4$Si(CH$_3$)$_3$ | |
| 3.075 | —CH(CH$_3$)CO—ON=C(CH$_3$)$_2$ | |
| 3.076 | —CH(CH$_3$)CO—ON=cyclopentyl | |
| 3.077 | —CH(CH$_3$)CO—ON=cyclohexyl | |
| 3.078 | -1,3-dioxolan-2-yleth-1-yl | |
| 3.079 | -1,3-dioxolan-2-ylmethyl | |
| 3.080 | -4-methyl-1,3-dioxolan-2-ylmethyl | |
| 3.081 | -1,3-dioxolan-2-ylpropyl | |
| 3.082 | -2-methyl-1,3-dioxolan-2-ylpropyl | |
| 3.083 | —C$_2$H$_4$C(OCH$_3$)$_2$ | |
| 3.084 | —C$_2$H$_4$C(OC$_2$H$_5$)$_2$ | |
| 3.085 | —CH(CH$_3$)C(OC$_2$H$_5$)$_2$ | |
| 3.086 | —CH(CH$_3$)C(OCH$_3$)$_2$ | |
| 3.087 | -2-methyl-1,3-dioxolan-2-ylmethyl | |
| 3.088 | —C$_2$H$_4$Si(OC$_2$H$_5$)$_3$ | |
| 3.089 | —CH$_2$Si(CH$_3$)$_3$ | |
| 3.090 | —CH(CH$_3$)Si(CH$_3$)$_3$ | |
| 3.091 | —C$_2$H$_4$Si(CH$_3$)$_3$ | |
| 3.092 | —CH(CH$_3$)CH$_2$Si(CH$_3$)$_3$ | |
| 3.093 | —CH(CH$_3$)PO(OC$_2$H$_5$)$_2$ | |
| 3.094 | —CH(CH$_3$)PO(CH$_3$)OC$_2$H$_5$ | |
| 3.095 | —CH(CH$_3$)CON(CH$_3$)SO$_2$CH$_3$ | |
| 3.096 | —CH(CH$_3$)CON(CH$_3$)SO$_2$CH$_2$Cl | |
| 3.097 | —CH$_2$CON(CH$_3$)SO$_2$CH$_3$ | |
| 3.098 | —CH(CH$_3$)CON(CH$_2$CH=CH$_2$)SO$_2$CH$_3$ | |
| 3.099 | —CH(CH$_3$)CON(cyclopropyl)SO$_2$CH$_3$ | |
| 3.100 | —CH(CH$_3$)CON[CH(CH$_3$)$_2$]SO$_2$CH$_3$ | |
| 3.101 | —CH$_2$COCH$_3$ | |
| 3.102 | —CH$_2$CO benzyl | |
| 3.103 | —CH$_2$CO phenyl | |
| 3.104 | —CH$_2$COCH$_2$OCH$_3$ | |
| 3.105 | —CH(CH$_3$)COCH$_3$ | |
| 3.106 | —CH(CH$_3$)COCH$_2$COOCH$_3$ | |
| 3.107 | —CH(COCH$_3$)COOC$_2$H$_5$ | |
| 3.108 | —CH(CH$_3$)COOCH(CH$_3$)CH$_2$SCH$_3$ | |
| 3.109 | —CH(CH$_3$)COOCH(CH$_3$)CH$_2$SC$_2$H$_5$ | |
| 3.110 | —CH(CH$_3$)COOCH(CH$_3$)CH$_2$SC$_3$H$_7$-n | |
| 3.111 | —CH(CH$_3$)COOCH(CH$_3$)CH$_2$SCH(CH$_3$)$_2$ | |
| 3.112 | —CH(CH$_3$)COOCH(CH$_3$)CH$_2$SC$_4$H$_9$-n | |
| 3.113 | —CH(CH$_3$)COOCH(CH$_3$)CH$_2$SC(CH$_3$)$_3$ | |
| 3.114 | —CH(CH$_3$)COOCH(CH$_3$)CH$_2$SCH(CH$_3$)C$_2$H$_5$ | |
| 3.115 | —CH(CH$_3$)CON(CH$_3$)CH$_2$CH(OCH$_3$)$_2$ | |
| 3.116 | —CH(CH$_3$)CON(CH$_3$)CH$_2$CH(OC$_2$H$_5$)$_2$ | |
| 3.117 | —CH(CH$_3$)COOC$_2$H$_4$OCH$_2$CH=CH$_2$ | |
| 3.118 | —CH(COCH$_3$)$_2$ | |
| 3.119 | —CH(CN)COOCH$_3$ | |
| 3.120 | —CH(OCH$_3$)COOCH$_3$ | |

TABLE 4

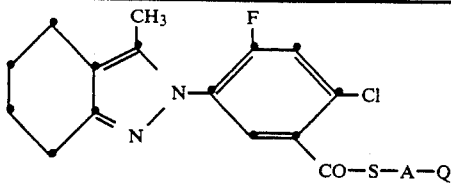

| No. | A—Q | phys. data |
|---|---|---|
| 4.001 | —CH$_2$—COOH | |
| 4.002 | —CH$_2$—COOCH$_3$ | $n_D^{24}$ 1,5832 |
| 4.003 | —CH$_2$—COOC$_2$H$_5$ | $n_D^{25}$ 1,5795 |
| 4.004 | —CH$_2$—COOC$_3$H$_7$-n | |
| 4.005 | —CH$_2$—COOCH(CH$_3$)$_2$ | |
| 4.006 | —CH$_2$—COOC$_4$H$_9$-n | |
| 4.007 | —CH$_2$—COOCH$_2$CH(CH$_3$)$_2$ | |
| 4.008 | —CH$_2$—COOCH(CH$_3$)C$_2$H$_5$ | |
| 4.009 | —CH$_2$—COOC(CH$_3$)$_3$ | |
| 4.010 | —CH$_2$—COO(CH$_2$)$_9$CH$_3$ | |
| 4.011 | —CH$_2$—COOCH$_2$CH$_2$OCH$_3$ | $n_D^{25}$ 1,5578 |
| 4.012 | —CH$_2$—COOCH$_2$CH$_2$OC$_2$H$_5$ | |
| 4.013 | —CH$_2$—COOCH$_2$CH$_2$OC$_3$H$_7$-n | |
| 4.014 | —CH$_2$—COO Cyclohexyl | |
| 4.015 | —CH$_2$—COOCH$_2$CH$_2$OCH$_2$CH=CH$_2$ | |
| 4.016 | —CH$_2$—COOC(CH$_3$)$_2$CN | |
| 4.017 | —CH$_2$COOCH$_2$CH$_2$SCH$_3$ | |
| 4.018 | —CH$_2$—COOCH(CH$_3$)CH$_2$N(CH$_3$)$_2$ | |
| 4.019 | —CH(CH$_3$)COOH | |
| 4.020 | —CH(CH$_3$)COOCH$_3$ | $n_D^{24}$ 1,5749 |
| 4.021 | —CH(CH$_3$)COOC$_2$H$_5$ | $n_D^{26}$ 1,5428 |
| 4.022 | —CH(CH$_3$)COOC$_3$H$_7$-n | $n_D^{21}$ 1,5491 |
| 4.023 | —CH(CH$_3$)COOCH(CH$_3$)$_2$ | $n_D^{26}$ 1,5394 |
| 4.024 | —CH(CH$_3$)COOC$_4$H$_9$-n | |
| 4.025 | —CH(CH$_3$)COOCH$_2$CH(CH$_3$)$_2$ | |
| 4.026 | —CH(CH$_3$)COOCH(CH$_3$)C$_2$H$_5$ | |
| 4.027 | —CH(CH$_3$)COOC(CH$_3$)$_3$ | |
| 4.028 | —CH(CH$_3$)COO—C$_5$H$_{11}$-n | |
| 4.029 | —CH(CH$_3$)COOCH$_2$CH$_2$OCH$_3$ | |
| 4.030 | —CH(CH$_3$)COOCH$_2$CH$_2$OC$_2$H$_5$ | |
| 4.031 | —CH(CH$_3$)COOCH$_2$CH$_2$OC$_3$H$_7$-n | |
| 4.032 | —CH(CH$_3$)COOCH$_2$CH$_2$OCH$_2$CH=CH$_2$ | |
| 4.033 | —CH(CH$_3$)COOC(CH$_3$)$_2$CN | |
| 4.034 | —CH(CH$_3$)COOCH$_2$CH$_2$SCH$_3$ | |
| 4.035 | —CH(CH$_3$)CH$_2$OH | |
| 4.036 | —CH(CH$_3$)CN | |
| 4.037 | —C$_2$H$_4$OH | |
| 4.038 | —CH(CH$_3$)CH$_2$Cl | |
| 4.039 | —C$_2$H$_4$Cl | |
| 4.040 | —CH$_2$CN | |
| 4.041 | —CH$_2$C(CH$_3$)$_2$OH | |
| 4.042 | —CH$_2$SCN | |
| 4.043 | —C$_2$C$_4$CN | |
| 4.044 | —CH(CH$_3$)CH$_2$CN | |
| 4.045 | —CH(CH$_2$OCH$_3$)COOCH$_3$ | |
| 4.046 | —CH$_2$CH(OCH$_3$)COOCH$_3$ | |
| 4.047 | —CH(CH$_3$)COOC$_2$H$_4$OCH$_2$CH=CH$_2$ | |
| 4.048 | —CH(CN)CH$_2$OCH$_3$ | |
| 4.049 | —CH$_2$CH(SCH$_3$)COOCH$_3$ | |
| 4.050 | —CH$_2$CH=CH$_2$ | |
| 4.051 | —CH$_2$CH=CHCl | |
| 4.052 | —CH$_2$CCl=CH$_2$ | |
| 4.053 | —CH$_2$CH=CHCN | |
| 4.054 | —CH$_2$C≡CH | |
| 4.055 | —CH$_2$C(CH$_3$)=CHCOOCH$_3$ | |
| 4.056 | —C$_2$H$_4$N(CH$_3$)$_2$ | |
| 4.057 | —C$_2$H$_4$-pyrolidino | |
| 4.058 | —C$_2$H$_4$-piperidino | |
| 4.059 | —C$_2$H$_4$-morpholino | |
| 4.060 | —CH[N(CH$_3$)$_2$]COOCH$_3$ | |
| 4.061 | —CH(CH$_3$)CH$_2$N(CH$_3$)$_2$ | |
| 4.062 | —CH(CH$_3$)CO-piperidino | |
| 4.063 | —CH(CH$_3$)CO-pyrrolidino | |
| 4.064 | —CH(CH$_3$)CO-4-methylpiperazino | |
| 4.065 | —CH(CH$_3$)CO-morpholino | |
| 4.066 | —CH(CH$_3$)CO-2-methymorpholino | |
| 4.067 | —CH(CH$_3$)CO-2,6-dimethylmorpholino | |
| 4.068 | —CH(CH$_3$)CO-2-methylpiperidino | |
| 4.069 | —CH(CH$_3$)CO-3-methylpiperidino | |
| 4.070 | —CH(CH$_3$)CO-4-methylpiperidino | |
| 4.071 | —CH(CH$_3$)CO—N(CH$_3$)CH$_2$CN | |
| 4.072 | —CH(CH$_3$)CO—N(CH$_2$CH=CH$_2$)$_2$ | |

TABLE 4-continued

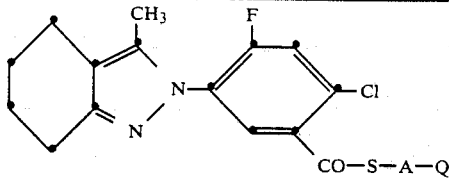

| No. | A—Q | phys. data |
|---|---|---|
| 4.073 | —CH(CH$_3$)CO—OCH$_2$Si(CH$_3$)$_3$ | |
| 4.074 | —CH(CH$_3$)CO—OC$_2$H$_4$Si(CH$_3$)$_3$ | |
| 4.075 | —CH(CH$_3$)CO—ON=C(CH$_3$)$_2$ | |
| 4.076 | —CH(CH$_3$)CO—ON=cyclopentyl | |
| 4.077 | —CH(CH$_3$)CO—ON=cyclohexyl | |
| 4.078 | -1,3-dioxolan-2-yleth-1-yl | |
| 4.079 | -1,3-dioxolan-2-ylmethyl | |
| 4.080 | -4-methyl-1,3-dioxolan-2-ylmethyl | |
| 4.081 | -1,3-dioxolan-2-ylpropyl | |
| 4.082 | -2-methyl-1,3-dioxolan-2-ylpropyl | |
| 4.083 | —C$_2$H$_4$C(OCH$_3$)$_2$ | |
| 4.084 | —C$_2$H$_4$C(OC$_2$H$_5$)$_2$ | |
| 4.085 | —CH(CH$_3$)C(OC$_2$H$_5$)$_2$ | |
| 4.086 | —CH(CH$_3$)C(OCH$_3$)$_2$ | |
| 4.087 | -2-methyl-1,3-dioxolan-2-ylmethyl | |
| 4.088 | —C$_2$H$_4$Si(OC$_2$H$_5$)$_3$ | |
| 4.089 | —CH$_2$Si(CH$_3$)$_3$ | |
| 4.090 | —CH(CH$_3$)Si(CH$_3$)$_3$ | |
| 4.091 | —C$_2$H$_4$Si(CH$_3$)$_3$ | |
| 4.092 | —CH(CH$_3$)CH$_2$Si(CH$_3$)$_3$ | |
| 4.093 | —CH(CH$_3$)PO(OC$_2$H$_5$)$_2$ | |
| 4.094 | —CH(CH$_3$)PO(CH$_3$)OC$_2$H$_5$ | |
| 4.095 | —CH(CH$_3$)CON(CH$_3$)SO$_2$CH$_3$ | |
| 4.096 | —CH(CH$_3$)CON(CH$_3$)SO$_2$CH$_2$Cl | |
| 4.097 | —CH$_2$CON(CH$_3$)SO$_2$CH$_3$ | |
| 4.098 | —CH(CH$_3$)CON(CH$_2$CH=CH$_2$)SO$_2$CH$_3$ | |
| 4.099 | —CH(CH$_3$)CON(cyclopropyl)SO$_2$CH$_3$ | |
| 4.100 | —CH(CH$_3$)CON[CH(CH)$_2$]SO$_2$CH$_3$ | |
| 4.101 | —CH$_2$COCH$_3$ | |
| 4.102 | —CH$_2$CO benzyl | |
| 4.103 | —CH$_2$CO phenyl | |
| 4.104 | —CH$_2$COCH$_2$OCH$_3$ | |
| 4.105 | —CH(CH$_3$)COCH$_3$ | |
| 4.106 | —CH(CH$_3$)COCH$_2$COOCH$_3$ | |
| 4.107 | —CH(COCH$_3$)COOC$_2$H$_5$ | |
| 4.108 | —CH(CH$_3$)COOCH(CH$_3$)CH$_2$SCH$_3$ | |
| 4.109 | —CH(CH$_3$)COOCH(CH$_3$)CH$_2$SC$_2$H$_5$ | |
| 4.110 | —CH(CH$_3$)COOCH(CH$_3$)CH$_2$SC$_3$H$_7$-n | |
| 4.111 | —CH(CH$_3$)COOCH(CH$_3$)CH$_2$SCH(CH$_3$)$_2$ | |
| 4.112 | —CH(CH$_3$)COOCH(CH$_3$)CH$_2$SC$_4$H$_9$-n | |
| 4.113 | —CH(CH$_3$)COOCH(CH$_3$)CH$_2$SC(CH$_3$)$_3$ | |
| 4.114 | —CH(CH$_3$)COOCH(CH$_3$)CH$_2$SCH(CH$_3$)C$_2$H$_5$ | |
| 4.115 | —CH(CH$_3$)CON(CH$_3$)CH$_2$CH(OCH$_3$)$_2$ | |
| 4.116 | —CH(CH$_3$)CON(CH$_3$)CH$_2$CH(OC$_2$H$_5$)$_2$ | |
| 4.117 | —CH(CH$_3$)COOC$_2$H$_4$OCH$_2$CH=CH$_2$ | |
| 4.118 | —CH(COCH$_3$)$_2$ | |
| 4.119 | —CH(CN)COOCH$_3$ | |
| 4.120 | —CH(OCH$_3$)COOCH$_3$ | |

FORMULATION EXAMPLES

EXAMPLE 2

Formulation Examples for compounds of formula I (percentages are by weight)

| (a) Wettable powders | (a) | (b) | (c) |
|---|---|---|---|
| compound of Tables 1 to 4 | 20% | 60% | 0.5% |
| sodium lignosulfonate | 5% | 5% | 5% |
| sodium laurylsulfate | 3% | — | — |
| sodium diisobutylnaphthalenesulfonate | — | 6% | 6% |
| octylphenol polyethylene glycol ether (7–8 moles of ethylene oxide) | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrates | (a) | (b) |
|---|---|---|
| compound of Tables 1 to 4 | 10% | 1% |
| octylphenol polyethylene glycol ether (4–5 moles of ethylene oxide) | 3% | 3% |
| calcium dodecylbenzenesulfonate | 3% | 3% |
| castor oil polyglycol ether (36 moles of ethylene oxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| compound of Tables 1 to 4 | 0.1% | 1% |
| talcum | 99.9% | — |
| kaolin | — | 99% |

Dusts which are ready for use are obtained by mixing the active ingredient with the carrier, and grinding the mixture in a suitable mill.

| (d) Extruder granulates | (a) | (b) |
|---|---|---|
| compound of Tables 1 to 4 | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| compound of Tables 1 to 4 | 3% |
| polyethylene glycol (mol. wt. 200) | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrates | (a) | (b) |
|---|---|---|
| compound of Tables 1 to 4 | 40% | 5% |
| ethylene glycol | 10% | 10% |
| nonylphenol polyethylene glycol ether (15 moles of ethylene oxide) | 6% | 1% |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| compound of Tables 1 to 4 | 5% |
| isopropylamine | 1% |
| octylphenol polyethylene glycol ether (78 moles of ethylene oxide) | 3% |
| water | 91% |

BIOLOGICAL EXAMPLES

EXAMPLE 3

Preemergence herbicidal action

In a greenhouse, immediately after sowing the test plants in seed dishes, the surface of the soil is treated with an aqueous dispersion of the test compounds, obtained from a 25% emulsifiable concentrate. Concentration ranges from 60 to 4000 g of test compound per hectare are applied. The seed dishes are kept in the greenhouse at 22°–25° C. and 50–70% relative humidity and the test is evaluated 3 weeks later. The state of the plants is assessed in accordance with the following rating:

1: plant has died or it has not germinated
2–3: very severe damage
4: severe damage
5: moderate damage
6: damage, the plant can recuperate
7–8: slight damage
9: normal growth, as untreated plants The compounds of tables 1 to 4 that were tested showed strong herbicidal action. The results obtained with compound 1.027 are summarized in Table 5.

TABLE 5

| | application rate g/ha | | | | |
|---|---|---|---|---|---|
| Plant | 2000 | 1000 | 300 | 250 | 125 |
| barley | 9 | 9 | 9 | 9 | 9 |
| wheat | 8 | 9 | 9 | 9 | 9 |
| maïze | 7 | 8 | 9 | 9 | 9 |
| sorghum | 7 | 7 | 9 | 9 | 9 |
| soya-bean | 9 | 9 | 9 | 9 | 9 |
| sun-flower | 7 | 8 | 9 | 9 | 9 |
| Abutilon | 1 | 1 | 4 | 4 | 5 |
| Sida spinosa | 1 | 1 | 4 | 4 | 5 |
| Amaranthus sp. | 1 | 1 | 1 | 1 | 1 |
| Chenopodium sp. | 1 | 1 | 1 | 1 | 1 |
| Solanum nigrum | 1 | 1 | 1 | 1 | 1 |
| Chrysanthemum leuc. | 1 | 1 | 1 | 1 | 1 |
| Viola tricolor | 1 | 1 | 1 | 1 | 1 |
| Veronica sp. | 1 | 1 | 1 | 1 | 1 |

EXAMPLE 4

Postemergence herbicidal action (selective weed control in cereal)

Barley, wheat, maïze and a number of weeds, are sprayed postemergence in the 4- to 6-leaf stage with an aqueous active ingredient dispersion at rates of 60 to 2000 g of test compound per hectare and kept at 24°–26° C. and 45–60% relative humidity. The test is evaluated 15 days later in accordance with the rating indicated above. The compounds of tables 1 to 4 that were tested showed good herbicidal action. Some results are shown in Tables 6 and 7.

TABLE 6 application rate 1000 g/ha

| | compound No. | | | | | | |
|---|---|---|---|---|---|---|---|
| Plant | 1.002 | 1.003 | 1.005 | 1.006 | 1.011 | 1.014 | 1.020 |
| barley | 6 | 6 | 7 | 8 | 6 | 8 | 7 |
| wheat | 7 | 7 | 8 | 8 | 7 | 9 | 7 |
| Abutilon | 1 | 1 | 1 | 1 | 1 | 1 | 1 |
| Sida spinosa | 1 | 2 | 1 | 1 | 4 | 4 | 1 |
| Chenopodium sp. | 2 | 3 | 1 | 1 | 2 | 4 | 1 |
| Solanum nigrum | 1 | 1 | 1 | 1 | 1 | 1 | 1 |
| Ipomoea purp. | 1 | 1 | 1 | 1 | 1 | 1 | 1 |
| Sinapis album | 1 | 1 | 1 | 2 | 1 | 3 | 1 |
| Chrysanthemum leuc. | 1 | 1 | 1 | 1 | 1 | 1 | 1 |
| Galium aparine | 3 | 1 | 1 | 4 | 4 | 2 | 2 |
| Viola tricolor | 3 | 1 | 1 | 1 | 1 | 1 | 1 |
| Veronica sp. | 1 | 1 | 1 | 1 | 1 | 1 | 1 |

| | compound No. | | | | | |
|---|---|---|---|---|---|---|
| Plant | 1.021 | 1.023 | 1.027 | 1.122 | 1.123 | 4.021 |
| barley | 7 | 6 | 8 | 7 | 6 | 6 |
| wheat | 6 | 7 | 8 | 7 | 6 | 7 |
| Abutilon | 1 | 1 | 1 | 1 | 1 | 1 |
| Sida spinosa | 1 | 1 | 4 | 1 | 1 | 1 |
| Chenopodium sp. | 1 | 1 | 2 | 1 | 1 | 1 |
| Solanum nigrum | 1 | 1 | 1 | 1 | 1 | 1 |

TABLE 6-continued

| | application rate 1000 g/ha | | | | | |
|---|---|---|---|---|---|---|
| Ipomoea purp. | 1 | 1 | 2 | 1 | 1 | 1 |
| Sinapis album | 1 | 1 | 1 | 1 | 1 | 4 |
| Chrysanthemum leuc. | 1 | 1 | 1 | 1 | 1 | 1 |
| Galium aparine | 2 | 1 | 3 | 4 | 4 | 4 |
| Viola tricolor | 2 | 1 | 1 | 1 | 1 | 1 |
| Veronica sp. | 1 | 4 | 3 | 1 | 1 | 1 |

TABLE 7

| | application rate 250 g/ha | | | | | | |
|---|---|---|---|---|---|---|---|
| | compound No. | | | | | | |
| Plant | 1.002 | 1.003 | 1.005 | 1.006 | 1.011 | 1.014 | 1.020 |
| barley | 8 | 8 | 8 | 9 | 8 | 8 | 8 |
| wheat | 8 | 9 | 9 | 9 | 9 | 9 | 8 |
| maïze | 6 | 6 | 8 | 7 | 6 | 7 | 6 |
| Abutilon | 2 | 1 | 1 | 1 | 1 | 1 | 1 |
| Sida spinosa | 3 | 3 | 4 | 4 | 4 | 4 | 3 |
| Chenopodium sp. | 3 | 4 | 4 | 4 | 3 | 4 | 2 |
| Solanum nigrum | 1 | 1 | 2 | 1 | 1 | 1 | 1 |
| Ipomoea purp. | 1 | 1 | 1 | 1 | 1 | 1 | 1 |
| Sinapis album | 3 | 2 | 1 | 2 | 3 | 3 | 5 |
| Chrysanthemum leuc. | 2 | 1 | 1 | 2 | 1 | 1 | 2 |
| Galium aparine | 3 | 2 | 4 | 4 | 4 | 4 | 2 |
| Viola tricolor | 4 | 1 | 1 | 1 | 3 | 1 | 4 |
| Veronica sp. | 2 | 1 | 2 | 3 | 1 | 4 | 1 |

| | compound No. | | | | | |
|---|---|---|---|---|---|---|
| Plant | 1.021 | 1.023 | 1.027 | 1.122 | 1.123 | 4.021 |
| barley | 8 | 8 | 8 | 8 | 7 | 7 |
| wheat | 8 | 9 | 9 | 8 | 8 | 8 |
| maïze | 7 | 7 | 8 | 6 | 6 | 6 |
| Abutilon | 1 | 1 | 3 | 1 | 1 | 1 |
| Sida spinosa | 3 | 4 | 5 | 1 | 1 | 1 |
| Chenopodium sp. | 3 | 1 | 3 | 4 | 1 | 1 |
| Solanum nigrum | 1 | 1 | 1 | 1 | 1 | 1 |

TABLE 7-continued

| | application rate 250 g/ha | | | | | |
|---|---|---|---|---|---|---|
| Ipomoea purp. | 1 | 1 | 2 | 1 | 1 | 1 |
| Sinapis album | 4 | 2 | 1 | 1 | 2 | 4 |
| Chrysanthemum leuc. | 2 | 2 | 1 | 1 | 1 | 1 |
| Galium aparine | 2 | 4 | 4 | 4 | 4 | 4 |
| Viola tricolor | 3 | 3 | 1 | 1 | 1 | 1 |
| Veronica sp. | 2 | 4 | 4 | 1 | 1 | 1 |

EXAMPLE 5

Selective herbicidal action in soya-beans

Soya-beans, grasses and weeds are reared in the greenhouse until they have reached after about 2 weeks the 4-leaf-stage. Then they are sprayed with a diluted broth of active substance. The treated plants are then kept in the greenhouse under optimal conditions for growth i.e. 26°-28° C. temperature, 43-60% relative humidity and regular watering. The test is evaluated 21 days after the treatment and the condition of the plants is assessed according to the rating given in example 3.

The compounds of tables 1 to 4 that were tested, showed tolerance towards the soya-plants and damaged the weeds. Some results are shown in Tables 8 and 9

TABLE 8

| | application rate 500 g/ha | | | | | | | |
|---|---|---|---|---|---|---|---|---|
| | compound No. | | | | | | | |
| Plant | 1.002 | 1.003 | 1.011 | 1.020 | 1.021 | 1.023 | 1.122 | 4.021 |
| soya-bean | 8 | 6 | 7 | 7 | 7 | 6 | 6 | 6 |
| sorghum sp. | 4 | 4 | 4 | 3 | 3 | 3 | 4 | 3 |
| Lolium perenne | 4 | 4 | 5 | 4 | 4 | 3 | 3 | 5 |
| Echinochloa | 4 | 4 | 5 | 5 | 3 | 4 | 4 | 4 |
| Abutilon | 1 | 1 | 1 | 1 | 1 | 1 | 1 | 1 |
| Sida spinosa | 3 | 2 | 4 | 1 | 2 | 1 | 1 | 1 |
| Xanthium | 3 | 1 | 1 | 2 | 4 | 3 | 3 | 4 |
| Amaranthus ret. | 2 | 4 | 4 | 2 | 2 | 1 | 1 | 4 |
| Chenopodium sp. | 2 | 3 | 2 | 2 | 1 | 1 | 1 | 1 |
| Solanum nigrum | 1 | 1 | 1 | 1 | 1 | 1 | 1 | 1 |
| Ipomoea purp. | 1 | 1 | 1 | 1 | 1 | 1 | 1 | 1 |
| Sinapis album | 1 | 2 | 2 | 4 | 3 | 1 | 1 | 4 |
| Chrysanthemum leuc. | 1 | 1 | 1 | 2 | 1 | 1 | 1 | 1 |
| Galium aparine | 3 | 2 | 4 | 2 | 2 | 4 | 3 | 4 |
| Viola tricolor | 3 | 1 | 1 | 2 | 2 | 1 | 1 | 2 |
| Veronica sp. | 1 | 1 | 1 | 1 | 2 | 1 | 1 | 4 |

TABLE 9

| | application rate 125 g/ha | | | | | | | |
|---|---|---|---|---|---|---|---|---|
| | compound No. | | | | | | | |
| Plant | 1.003 | 1.005 | 1.006 | 1.011 | 1.014 | 1.023 | 1.122 | 1.123 | 4.021 |
| soya-bean | 7 | 8 | 8 | 7 | 7 | 8 | 7 | 7 | 7 |
| Abutilon | 1 | 1 | 1 | 1 | 1 | 1 | 1 | 1 | 1 |
| Xanthium | 1 | 2 | 2 | 1 | 3 | 4 | 4 | 4 | 4 |
| Solanum nigrum | 1 | 2 | 2 | 1 | 2 | 1 | 3 | 1 | 1 |
| Ipomoea purp. | 1 | 1 | 1 | 1 | 2 | 1 | 1 | 1 | 1 |
| Chrysanthemum leuc. | 1 | 1 | 3 | 2 | 2 | 2 | 1 | 1 | 1 |
| Galium aparine | 2 | 4 | 4 | 4 | 4 | 4 | 4 | 4 | 4 |
| Viola tricolor | 1 | 2 | 1 | 3 | 2 | 4 | 1 | 1 | 2 |
| Veronica sp. | 1 | 4 | 4 | 3 | 4 | 4 | 1 | 1 | 4 |

EXAMPLE 6

Preemergence herbicidal action

Plastic pots are filled with expanded vermiculite (density: 0.135 g/cm$^3$; water-absorbing capacity: 0.565 l/l). After the non-adsorptive vermiculite has been saturated with an aqueous emulsion in deionised water which contains the test compound in a concentration of 70.8 ppm, seeds of the following plants are sown on the surface: Nasturtium officinalis, Agrostis tenuis, Stellaria media and Digitaria sanguinalis. The pots are then kept in a climatic chamber at 20° C., an illumination of about 20 klux and a relative humidity of 70%. During the germinating phase of 4 to 6 days, the pots are covered with lightpermeable material and watered with deionised water to increase the local humidity. After the 5th day, 0.5% of a commercial liquid fertiliser (Greenzit ®) is added to the water. The test is evaluated 12 days after sowing and the action on the test plants is assessed. The tested compounds of Tables 1 to 4 exhibit good to very good herbicidal activity.

EXAMPLE 7

Herbicidal action in rice (paddy rice)

Rice and the weeds Scirpus sp. and Monocharia vag., which occur in water, are sown in plastic beakers (surface: 60 cm$^2$; volume: 500 ml). After sowing, the beakers are filled with water up to the surface of the soil. 3 days after sowing, the water level is increased to slightly above the soil surface (3-5 mm). Application is effected 3 days after sowing by spraying the beakers with an aqueous emulsion of the test compounds. The rate of application corresponds to a concentration of 0.5 kg of active ingredient per hectare (concentration of the spray mixture = 550 l/ha). The beakers are then kept in the greenhouse under optimum growth conditions for rice weeds, i.e. at 25°-30° C. and at high humidity. The evaluation of the tests takes place 3 weeks after application. The state of the plants is assessed in accordance with the rating indicated above. The tested compounds of tables 1 to 4 showed good herbicidal action on the weeds while being tolerant towards the rice plants.

EXAMPLE 8

Desiccation and defoliation action

Cotton plants of the Deltapine variety are reared in earthen-ware pots in a greenhouse. After the capsules have formed, the plants are sprayed with an aqueous formulation of compound No. 1 at rates of application corresponding to 1.2, 0.6 and 0.3 kg/ha in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant).

In this test, plants treated with compounds of Tables 1 to 4 at rates of application of 0.6 and 1.2 kg/ha are left after 7 days with only a few dried out leaves (>80% defoliation and dessication).

EXAMPLE 9

Growth inhibition of grasses and clover

A mixture of grasses Poa, Festuca, Lolium, Bromus, Cynosurus and of clover (Trifolium pratense and repens) are sown in 15 cm plastic pots filled with sterile garden soil and reared in a greenhouse at a day temperature of 21° C. and a night temperature of 17° C. Lighting was 13.5 hours daily at at least 7000 Lux. After emergence the plants were cut back each week to 6 cm hight. About 42 days after sowing and one day after the last cut, the plants are sprayed with an aqueous mixture of a compound of Tables 1 to 4 in an application between 0.3 and 3 kg/ha, which was prepared by dilution of a 25% wettable powder at an amount of water corresponding to 500 l/ha.

The test was evaluated 3 weeks after the treatment. The hight of the regrowth was measured and compared to the average regrowth of not treated control plants. The compounds of Tables 1 to 4 that were tested reduced the regrowth by 10 to 80%.

We claim:

1. A 5-(pyrazol-1-yl)-benzoic acid-thiol ester of the formula I

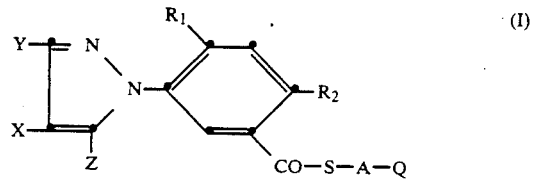

wherein
X is hydrogen or halogen,
Y is $C_1$-$C_4$alkyl
X and Y together with the carbon atoms, to which they are bound, form also a 5- to 6-membered ring, which can be substituted by methyl
Z is halogen, $C_1$-$C_6$alkyl, $C_1$-$C_4$alkoxy or $C_1$-$C_4$alkylthio
$R_1$ is hydrogen or halogen,
$R_2$ is halogen,
A is a straight chain or branched $C_1$-$C_4$alkylene bridge, which is unsubstituted or mono- or polysubstituted by $C_1$-$C_4$alkoxy, $C_1$-$C_4$alkylthio or cyano.

2. A 5-[2-(4,5,6,7-tetrahydro-2H-indazolyl)]-benzoic acid-thiolester according to claim 1 of the formula

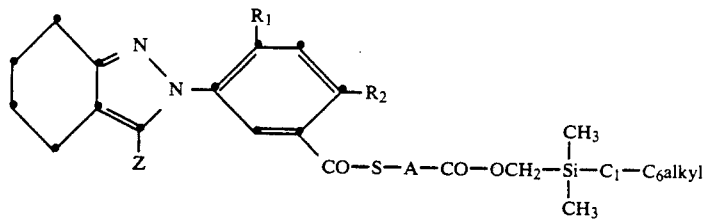

wherein A, $R_1$, $R_2$ and Z have the meaning given in claim 1.

3. 5-[2-(3-Chloro-4,5,6,7-tetrahydro-2H-indazolyl)]-2-chloro-4-fluorobenzoic acid-(trimethylsilylmethylthio)ester according to claim 1.

4. A herbicidal and plant-growth-regulating composition, which contains, beside inert carrier material and other additives as active component, a herbicidally and growth-regulating effective amount of a 5-(pyrazol-1-yl)-benzoic acid-thiolester according to claim 1.

5. A method for controlling in pre- or postemergent application, weeds in crops of culture plants, which comprises treating the culture plant or the crop area, with an effective amount of a compound according to claim 1, or with a composition containing such a compound.

6. A method for the desiccation and defoliation of crops of cotton and potatoes, in order to facilitate mechanical harvest, which comprises treating the culture, shortly before harvest, with an effective amount of a compound according to claim 1, or with a composition containing such a compound.

* * * * *